United States Patent [19]

Harris et al.

[11] Patent Number: 5,132,345

[45] Date of Patent: Jul. 21, 1992

[54] ION-SELECTIVE ELECTRODES

[76] Inventors: Stephen J. Harris, 10 Broadford Crescent Ballinteer, Dublin 16, Ireland; Michael A. McKervey, 27a Osborne Park, Belfast BT9 6JN, Northern Ireland; Gyula Svehla, 13 Hillcrest, Carrigaline, County Cork; Dermot Diamond, Coolquoy, The Ward, County Dublin, both of Ireland

[21] Appl. No.: 624,623

[22] Filed: Dec. 10, 1990

[51] Int. Cl.$^5$ .................. C08J 5/22; G01N 27/31
[52] U.S. Cl. .................. 524/108; 204/415; 204/416; 204/418; 525/333.4; 525/359.2; 525/385; 526/194; 526/204; 526/208; 526/209; 528/12; 528/33; 528/59; 528/373; 528/392; 549/347; 556/419; 556/437; 556/446; 556/449
[58] Field of Search .............. 524/108; 204/415; 549/347; 556/419

[56] References Cited

U.S. PATENT DOCUMENTS

| | | |
|---|---|---|
| 4,447,585 | 5/1984 | Parker . |
| 4,523,994 | 6/1985 | Shono et al. . |
| 4,531,007 | 7/1985 | Toke et al. . |
| 4,554,362 | 11/1985 | Shono et al. . |
| 4,556,700 | 12/1985 | Harris et al. . |
| 4,642,362 | 2/1987 | Harris et al. ............... 556/419 |
| 4,699,966 | 10/1987 | Harris et al. ............... 528/12 |
| 4,866,198 | 9/1989 | Harris . |
| 4,882,449 | 11/1989 | Harris .................. 556/419 |
| 4,908,399 | 3/1990 | Harris .................. 524/243 |
| 4,933,407 | 6/1990 | Harris .................. 526/208 |

FOREIGN PATENT DOCUMENTS 01-250750 10/1989 Japan .

OTHER PUBLICATIONS

C. Gutsche "Calixarenes. 4. The Synthesis, Characterization & Properties of the Calixarenes from p-tert-Butylphenol" J. Am. Chem. Soc 103 (1981) 3782.

Cadogan et al, Irish Chemical News, ISSN 07904975, Aug. 1990.

Cadogan et al, "Sodium-selective Polymeric Membrane Electrodes Based on Balix(4)arene Ionophores", Analyst, vol. 114 (Dec. 1989) 1551–1554.

Cadogan et al "Caesium-selective Poly(vinyl chloride) Membrane Electrodes Based on Calix(6)arene Esters", Analyst, vol. 115 (Sep. 1990) 1207–1210.

Kimura et al "Polymeric Membrane Sodium-Selective Electrodes Based on Lipophilic Calix(4)arene Derivatives", Anal. Chem. 62, (1990) 1510–1513.

Pretsch et al "Design Features of Ionophores for Ion Selective Electrodes:" Pure & Appl. Chem, vol. 60, No. 4 (1988) 567–574.

Diamond et al, Analytica Chimica Acta, 204 (1988) 223–231.

Arnaud-Neu et al, "Synthesis, X-ray Crystal Structures and Cation-Binding Properties of Alkyl Calixyaryl Esters and Ketones, a New Family of Macrocyclic Molecular Receptors", J. Am. Chem. Soc. (1989) 111, 8681–8691.

Kimura et al "Lipophilic Calix(4)arene Ester and Amide Derivatives as Neutral Carriers for Sodium Ion-Selective Electrodes", Chem Lett (1988) pp. 615–616.

C. Gutsche et al "Calixarenes", Acc. Chem. Res 103 (1983) 161–170.

Primary Examiner—Joseph L. Schofer
Assistant Examiner—Fred Zitomer
Attorney, Agent, or Firm—Vidas & Arrett

[57] ABSTRACT

An ion-selective polymeric membrane for an electrochemical sensor for use in analytical chemistry, comprising a) a supporting matrix e.g. of PVC, and
b) an ionophore selected from calixarene or oxacalixarene derivatives of the formula IV

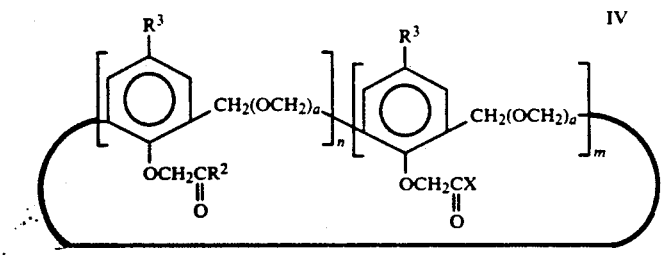

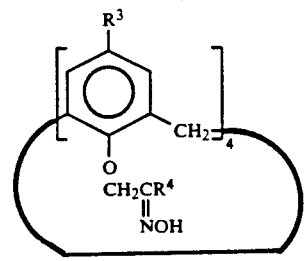

wherein
n+m=3-8;
m=0-8;
n=0-8;
a, which may be the same or different on each aryl group, is 0 or 1;
$R^2$ is alkyl, aryl, alkaryl, alkoxy, alkoxyalkoxy, aryloxy, alkaryloxy, alicyclic, alkylthio, arylthio, alkarylthio, or a substituted derivative thereof;
$R^3$ is —H, alkyl or alkenyl;
X is —OH or a group containing an acrylate or methacrylate functional group;
provided that when X is —OH, n is at least $\frac{1}{2}$(n+m);
and provided that when m=0, n=4, a=0 and $R^3$ is alkyl or allyl, $R^2$ is not alkoxy having 4 or more carbon atoms in the alkyl group;
and provided that when m=0, n=4, a=0 and $R^3$ is t-butyl, $R^2$ is not methoxy or ethoxy;

or of the formula V wherein $R^4$ is alkyl; or polymers of those compounds of the formula IV in which X is a group containing an acrylate or methacrylate group.

New compounds in which $R^2$ is —$SCH_2CH_3$ are described.

Selectivity coefficients and slope measurements are given for the ionophores in PVC electrodes which are selective for sodium, potassium and caesium.

17 Claims, 1 Drawing Sheet

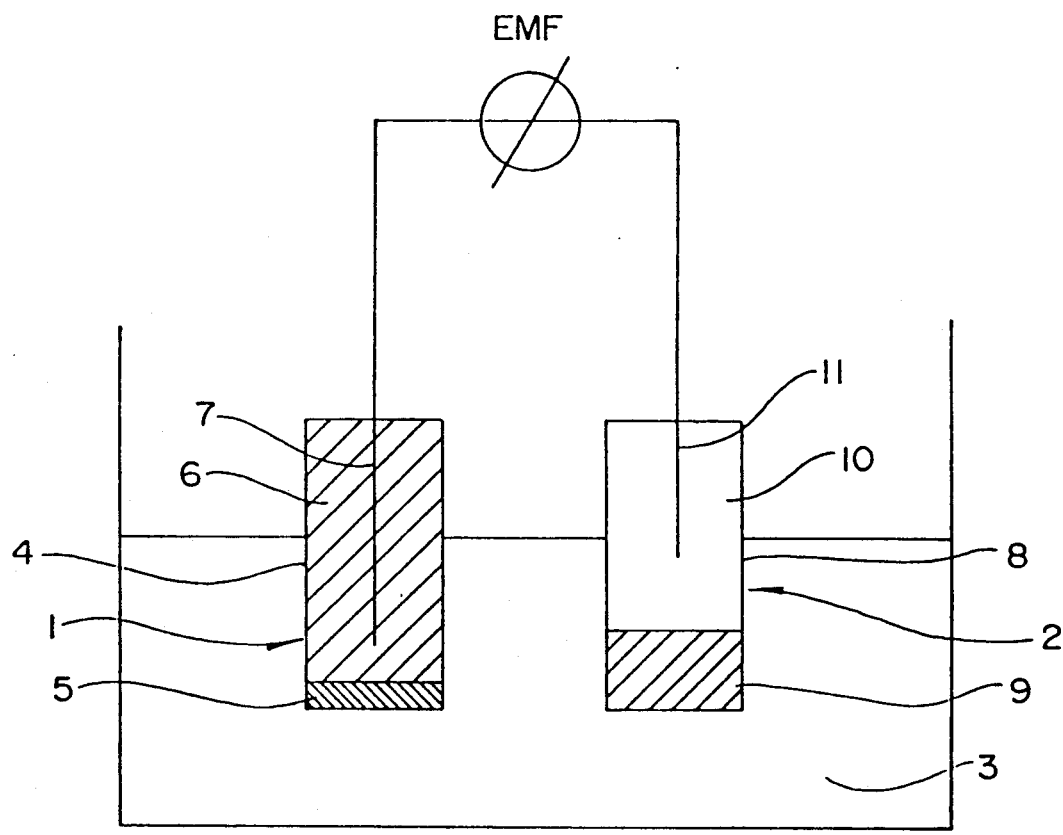

ION-SELECTIVE ELECTRODES

BACKGROUND OF THE INVENTION a) Field of the Invention

This invention relates to ion-selective polymeric membranes for use in electrochemical sensors such as ion-selective electrodes, coated wire electrodes or ion-selective field effect transistors, with applications in analytical chemistry, particularly in clinical and environmental chemistry.

Such devices are electrochemical sensors that allow potentiometric determination of the activity of certain ions in the presence of other ions; the sample under test is usually an aqueous solution. Such a device constitutes a galvanic half-cell, consisting of an ion-selective membrane, an internal contacting solution (optional), and an internal reference electrode. The other half cell is given by an external reference electrode dipping into a reference electrolyte.

In the ideal case, the ion-selective membrane should be permeable only to the analyte ion but non-permeable to all other ions including the analyte counterion. One of the families of membranes under investigation is that in which the membranes contain neutral molecular carriers, namely uncharged lipophilic molecules. These molecules are capable of selectively transporting the analyte ion across a hydrophobic membrane (see "Design features of ionophores for ion selective electrodes", Pretsch et. al., Pure & Appl. Chem., Vol. 60, No. 4 pp567-574, 1988).

b) Description of the Related Art

Use of crown ether compounds in ion-selective electrodes has been proposed (see U.S. Pat. Nos. 4,531,007 Toke et. al: 4,544,362 Shono et. al; and 4,523,994 Shono et. al).

Investigations have also been carried out into the use of calixarene-based ionophores.

Diamond et. al., Analytica Chimica Acta, 204 (1988) 223-231 described a sodium-selective electrode based on the ligand methyl p-t-butylcalix(4)arene acetate. Solutions of this ionophore produced sodium-selective electrodes both in the form of single liquid membranes and when incorporated into PVC membranes. Exchanger anions (TClPB) were included to reduce membrane resistance and to obtain the desired Na+ selectivity. It was reported that ethyl p-t-butylcalix(4)arene acetate, ethyl p-t-butylcalix(6)arene acetate and ethyl calix(6)arene acetate had produced working liquid membrane electrodes, with the tetramer being Na+ selective and the hexamers being caesium-selective. However no experimental results were reported for electrodes made with these ligands.

Arnaud-Neu et. al., J. Am. Chem. Soc. 1989, 111, 8681-8691 described ionophoric activity of a group of alkyl calixaryl esters and ketones. Stability constants were determined for the alkali-metal cation complexes of the tetrameric ethyl acetate, the hexameric ethyl acetate, the tetrameric methyl ketone, the tetrameric tert- butyl ketone and the tetrameric phenyl ketone, all being p-tert.-butyl derivatives. However, this publication provided no further teaching about ion-selective electrodes and merely reported the work of Diamond et. al., Anal. Chim. Acta. 1988, 204, 223 mentioned above.

Kimura et. al., Chem. Lett. 1988, 615 described PVC-based membrane electrodes based on decyl p-t-butylcalix(4)arene acetate and p-t-butylcalix(4)arene dibutylamide.

Japanese Patent Publication JP 01,250,750 (89,250,750) Shono et. al., in CA Selects: Synthetic Macrocyclic Compounds, Issue 15, 1990. page 9, Item 113:17168k described a sodium ion-selective membrane electrode containing as a neutral carrier at least one compound of the formula III

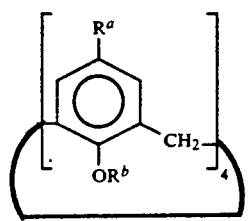

where
$R^a$ = alkyl, allyl
$R^b$ = $CH_2COOR^c$, $CH_2CONR_2^c$
$R^c$ = hydrophobic hydrocarbon having 4 or more carbon atoms.

An ionophore suitable for an ion-selective electrode should have the following properties:
1. Polar groups capable of replacing the hydration shell of the ion that it will complex;
2. High solubility in non-polar solvents and it must be insoluble in water;
3. A cavity of optimum diameter to hold the target ion;
4. The complex formed should remain in the membrane phase;
5. Complex formation which is fast and reversible.

SUMMARY OF THE INVENTION

The present inventors have now found calixarene derivatives and oxacalixarene derivatives which show unexpected or unpredictable behaviour in meeting these criteria.

The present invention provides a membrane for an ion-selective polymeric membrane electrode comprising
a) a supporting matrix, and
b) an ionophore selected from calixarene or oxacalixarene derivatives of the formula IV

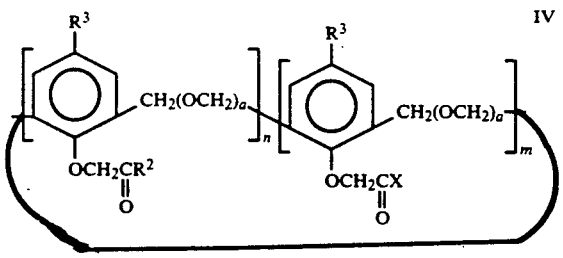

wherein
$n + m = 3-8$;
$m = 0-8$;
$n = 0-8$;
a, which may be the same or different on each aryl group, is 0 or 1;
$R^2$ is alkyl aryl, alkaryl, alkoxy, alkoxyalkoxy, aryloxy, alkaryloxy, alicyclic, alkylthio, arylthio, alkarylthio, or a substituted derivative thereof;
$R^3$ is —H, alkyl or alkenyl;
X is —OH or a group containing an acrylate or methacrylate functional group;

provided that when X is —OH, n is at least ½ (n+m);

and provided that when m=0, n=4, a=0 and R³ is alkyl or allyl, R² is not alkoxy having 4 or more carbon atoms in the alkyl group;

and provided that when m=0, n=4, a=0 and R³ is t-butyl, R² is not methoxy or ethoxy;

or of the formula V

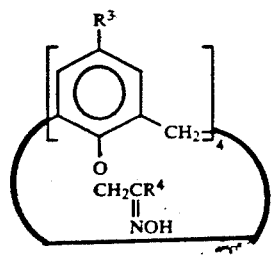

V wherein R⁴ is alkyl; or polymers of those compounds of the formula IV in which X is a group containing an acrylate or methacrylate group.

In a preferred group of compounds, R² is —[O(CH₂)$_{n'}$]$_{n''}$O C$_{m'}$ H$_{2m'+1}$ wherein n' = 1-5, preferably 2
m' = 1-5, preferably 1, 2 or 4
n" = 0 or 1, preferably 1.

In another preferred group of compounds R² is —[OCH₂C(O)]$_{n''}$—C₆H₅ wherein n" is as defined above.

In a further preferred group of compounds, R² is —SC$_{m'}$H$_{2m'+1}$ wherein m' is as defined above.

The compounds of formula IV wherein R² is an alkylthio, arylthio or alkarylthio group, or a substituted derivative thereof are novel compounds and are also claimed herein.

In a preferred group of compounds when R³ is H, R² is —OC$_{m'}$H$_{2m'+1}$ wherein m' is as defined above.

In the compounds of formula IV, m is preferably 0 to 1. If X is a group containing an acrylate or methacrylate functional group, said group is preferably of the formula

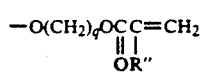

wherein
q = an integer 2-10 and
R" is H or CH₃.

Due to the (meth)acrylate functionality, such compounds are capable of free radical polymerisation.

Calixarene and oxacalixarene derivatives have a cup-like conformation with a cavity into which the metal ion is bound. Generally such derivatives have a cone conformation in which all of the phenolic moieties point in the same direction but some compounds may have a partial cone conformation in which one phenolic moiety points in the opposite direction to the others.

For a sodium-selective membrane, it is preferred to use calixarene derivatives of the formula VI$^a$

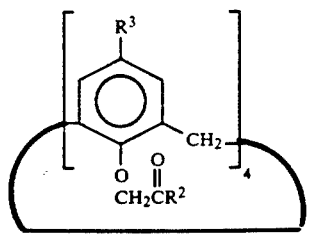

VI$^a$ in cone conformation, wherein R² and R³ are as defined above, or of the formula VII

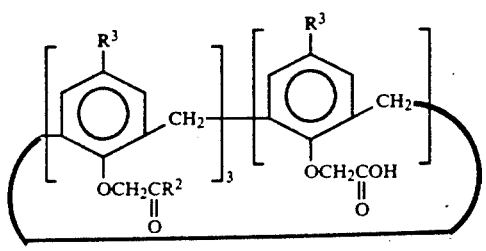

VII wherein R² and R³ are as defined above.

For a potassium-selective membrane, it is preferred to use calixarene derivatives of the formula VI$^b$

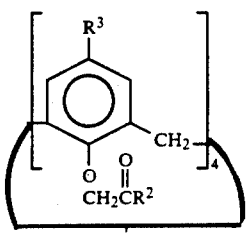

VI$^b$ in partial cone conformation, wherein R² and R³ are as defined above, or oxacalixarene derivatives of the formula VIII$^a$

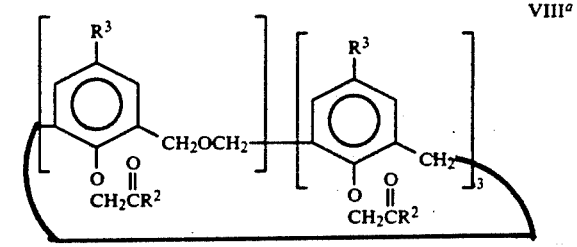

VIII$^a$

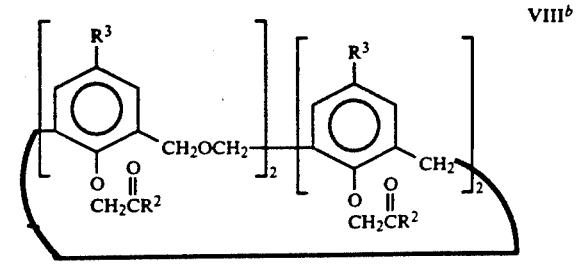

VIII$^b$

-continued

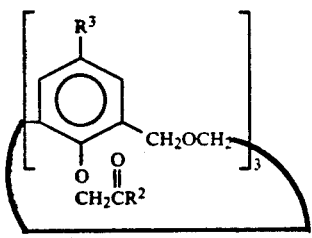
VIII<sup>c</sup> wherein R² and R³ are as defined above.

For a caesium-selective membrane it is preferred to use calixarene derivatives of the formula IX<sup>a</sup>

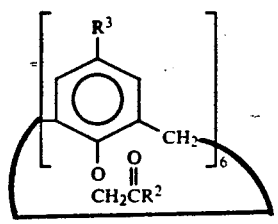
IX<sup>a</sup> or of the formula IX<sup>b</sup>

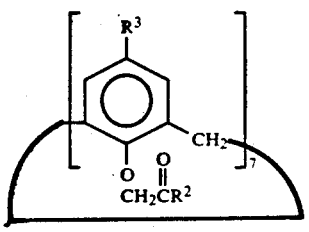
IX<sup>b</sup> or of the formula IX<sup>c</sup>

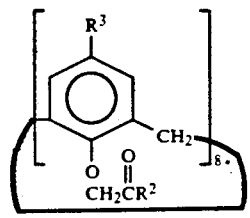
IX<sup>c</sup> wherein R² and R³ are as defined above.

The supporting matrix for the membrane electrode is preferably poly(vinylchloride) (PVC). Other polymeric materials such as silicon polymers may also be used—see "Ion-Selective Electrode Reviews", Vol. 5, 1983, p3–90, D. Ammann et. al.

The composition for the membrane electrode will also normally contain an ion-exchanger to reduce membrane resistance (preferably by approx. one order of magnitude to approx. one megaohm) and to reduce anion interference—see "Ion-Selective Electrode Reviews", Vol. 5, 1983, p3–90 as cited above; and also Anal. Chim. Acta., 204 (1988) 223–231. The preferred exchanger is potassium tetra-parachlorophenyl borate (KTpClPB) but other related compounds having large lipophilic anions may also be suitable. The exchanger may however be omitted when certain cations are targetted.

The composition will also normally contain a plasticiser which may have two functions: a) to plasticise the PVC or other polymer and b) to serve as an inert solvent for the ligand. The preferred plasticiser is 2-nitrophenyl octyl ether but other plasticisers such as dioctylphthalate, dibutylsebacate or dioctylphenylphosphonate may also be used.

Alkyl or alkenyl groups shall preferably contain from 1 to 10 carbon atoms, more preferably from 1 to 5 carbon atoms, and aryl and alkaryl groups shall preferably have from 6 to 20 carbon atoms, more preferably from 6 to 10 carbon atoms. A substituted derivative of the foregoing may suitably be substituted with one or more halo groups or radicals containing nitrogen or substituted or interrupted by one or more oxo groups. Radicals containing nitrogen may or may not form part of a heterocyclic ring; a suitable radical may contain an amino or amide group, or may be a heterocyclic ring which may be saturated or unsaturated, aliphatic or aromatic, for example a 5- or 6-membered ring containing 1 or 2 nitrogen atoms. Reference is directed to U.S. Pat. No. 4,882,449 Harris, the contents of which are incorporated herein by reference. Halogen may be chlorine, bromine, fluorine or iodine.

The preparation of calixarene derivatives is known and is described, for example, in C. Gutsche et. al., Acc. Chem. Res., 16, 161–170 (1983); in U.S. Pat. Nos. 4,556,700 Harris et. al., 4,866,198 Harris, and 4,882,449 Harris and in J. Inclusion Phenomena 2 199–206 (1984) D. Reidel Publishing Company; the appropriate disclosures of all of which are incorporated herein by reference.

The preparation of aryl calixarene derivatives is described in European Patent Publication No. 0,259,016 (Application No. 87 306 963.7) and equivalent applications in other countries.

Mixed functionality calixarene derivatives are described in European Patent Publication No. 0,196,895 A2 and U.S. Pat. No. 4,642,362 Harris et. al. When m is greater than or equal to 2 in the compounds of formula IV, the aryl groups having the —OCH₂C(O)X side chain may be interspersed around the ring between the aryl groups having the —OCH₂C(O)R² side chain.

In the oxacalixarene derivatives of formula IV when a is 1 on more than one aryl group, the methylene and ether bridges may or may not alternate within the oxacalixarene molecule.

Oxacalixarene compounds may be readily synthesised by methods described in C. Gutsche et. al., J. Am.-Chem. Soc. 103, 3782 (1981); B. Dhawan et. al., J. Org. Chem., 48, 1536 (1983), U.S. Pat. Nos. 4,098,717 Buriks et. al., 4,933,407 Harris et. al., and European Patent Publication No. 0,309,291 (Application No. 88 308 897.3) the appropriate disclosures of which are incorporated herein by reference.

Calixarene and oxacalixarene derivatives may usefully be polymerbound by methods described in U.S. Pat. Nos. 4,642,362 Harris et. al., or 4,699,966 Harris et. al., or by methods analogous to those described for crown ethers in U.S. Pat. No. 4,447,585 Parker or Tetrahedron 36 461–510 (1980). The derivatives may also be silica gel bound by methods analogous to those described in J. Incl. Phenomena 7 127–136 (1989) or J. Chem. Soc. Chem. Comm. 812 (1988).

BRIEF DESCRIPTION OF THE DRAWINGS

The drawing is a schematic diagram of a potentiometric measuring cell.

As shown in the drawing, the cell comprises an ion-selective electrode 1 and a reference electrode 2 immersed in a aqueous sample solution 3. The ion selective electrode 1 comprises an electrode body 4, an ion selective membrane 5, an internal filling solution 6 and an internal reference electrode 7. The reference electrode 2 comprises an electrode body 8, a diaphragm 9, a reference electrolyte 10 and an external reference electrode 11.

An internal filling solution is not essential and may be omitted in a solid state device involving, for example, coated wire devices, planar versions of electrodes or ion-selective field effect transistors. In each case, the signal will be produced by the ion-selective membrane and will depend mainly on the properties of the ionophore (neutral carrier) used.

DESCRIPTION OF THE PREFERRED EMBODIMENTS

Embodiments of the invention are described below by way of example.

EXAMPLE 1

Preparation: Tetraethoxyethyl p-tert.-butylcalix(4)arene tetraacetate—XI

To 2.38 g (0.0025 mole) of p-t-butylcalix(4)arene tetra-acetyl chloride prepared by reaction of carboxylic acid tetramer described in European Patent Publication No. 0,259,016 (Application No. 87 306 963.7) with thionyl chloride, in 10 mls dry THF under nitrogen was added 1.6 g (0.02 mole) pyridine and 1.8 g (0.02 mole) ethoxyethanol at room temperature with stirring to give an off white solid precipitate. The reaction mixture was stirred for a further 17 hours at room temperature, then all volatiles were removed under reduced pressure with warming to give 2.9 g (100%) colourless oil product which was taken up in 25 mls dichloromethane then washed with distilled water then dried over dried magnesium sulphate to give 2.8 g (97%) colourless oil which was chromatographed on basic alumina with dichloromethane as eluent to give high purity product Compound XI as a colourless oil.

i.r. spectroscopy $\nu$ 1760 (S) cm$^{-1}$ C=0 which was shown by HPLC analysis to be 92% pure. Retention time 17.60 minutes 1.5 mls/min 280 nm Radpak C18 THF/H$_2$O 25-100%.

EXAMPLE 2

Preparation: Tetra methoxyethyl p-tert.-butylcalix(4)arene tetraacetate—XII

To 2.38 g (0.0025 mole) of p-t-butylcalix(4)arene tetra-acetyl chloride prepared as in Example 1 was added 1.6 g (0.02 mole) pyridine and 1.52 g (0.02 mole) methoxyethanol at room temperature with stirring; a white solid formed. The reaction mixture was stirred for 24 hours at room temperature, then all volatiles were removed, the last traces at reduced pressure to give a solid which was taken up in 25 mls dichloromethane which was then washed well with water, then dried over dried magnesium sulphate to give after removal of volatiles 2.5 g (90%) colourless oil which crystallised on standing overnight to give colourless solid Compound XII mp 83°-7° C. recrystallised from ethanol/water and then recrystallised from methoxyethanol to give a solid, mp 109°-110° C.

Elemental Analysis calculated for $C_{64}$ $H_{88}$ $O_{16}$ C=69.06, H 7.91, O 23.07; Found C=69.02, H 7.90, O 23.08. i.r. spectroscopy $\nu$ 1743 (S) cm$^{-1}$. C=0.

EXAMPLE 3

Preparation: Tetra-n.butoxyethyl p-tert.-butylcalix(4)arene tetraacetate—XIII

To 2.38 g (0.0025 mole) p-t-butyl calix(4)aryl tetraacetyl chloride prepared as in Example 1 was added 1.6 g (0.02 mole) pyridine and 2.4 g (0.02 mole) n-butoxyethanol at room temperature with stirring to give an off white solid suspension. The reaction mixture was allowed to stir overnight for 17 hours at room temperature, then all volatiles were removed under reduced pressure with heat applied to give 3.6 g oil product which was taken up in 25 mls dichloromethane which was washed well with distilled water then dried over dried magnesium sulphate to give 3.4 g (93%) colourless oil which was chromatographed on basic alumina with dichloromethane as eluent to give high purity product Compound XIII as a colourless oil.

i.r. $\nu$ 1760 (S) cm$^{-1}$ C=0 which was shown by HPLC analysis to be 87+% pure. Retention time 18.58 minutes 1.5 mls/min 280 nm Radpak C18 THF/H$_2$O 25-100%.

EXAMPLE 4

Preparation: Tetrabenzyl calix(4)arene tetraacetate—XIV

To 3.18 g calix(4)arene (0.0075 mole) in 90 mls dry acetone was added 6.2 g (0.045 mole) potassium carbonate anhydrous and 13.7 g (0.060 mole) benzyl 2-bromoacetate and the entire was refluxed under nitrogen for 6 days. The volatiles were then removed under reduced pressure and taken up in 75 mls dichloromethane which was then washed well with 5% aqueous HCl, then distilled water. The organic layer was dried over dried magnesium sulphate and filtered, then volatiles were removed from the filtrate to give 6.5 g (85%) off white solid product which was recrystallised from ethanol/dichloromethane to give 4.7 g colourless crystalline Compound XIV, all cone conformation by nmr analysis.

i.r. spectroscopy results $\nu$ 1750 (S) C=0 cm$^{-1}$.

EXAMPLE 5

Preparation: Tetra tert.-butyl calix(4)arene tetraacetate—XV

To 3.18 g calix(4)arene (0.0075 mole) in 85 mls dry acetone was added 6.2 g (0.045 mole) potassium carbonate anhydrous and 11.7 g (0.060 mole) t-butyl bromoacetate and the entire was refluxed under nitrogen for 6 days. The volatiles were then removed under reduced pressure and taken up into 50 mls dichloromethane which was washed well with 1% aqueous HCl then distilled water. The organic layer was dried over dried magnesium sulphate and filtered, then volatiles were removed from the filtrate to give off white 5.9 g solid crude tetraester 90% yield. Recrystallisation from ethanol gave 1.3 g colourless crystals of Compound XVa which appeared to be of partial cone conformation from Hnmr analysis V Complex Spectrum mp 154°-9° C.

i.r. spectroscopy $\nu$ 1747 (S) 1720 Sh(S) cm$^{-1}$ C=0. The 2.0 g colourless compound that was insoluble in ethanol was identified as the all cone product compound XVb mp 270°-3° C. Nmr (CDCl$_3$)(RT): AB quartet 3.2, 4.9 and one t-butyl singlet resonance 1.5 ppm.

i.r. spectroscopy $\nu$ 1740 (S) cm$^{-1}$ C=0. Elemental Analysis (calculated for $C_{52}$ $H_{64}$ $O_{12}$: C=70.88, H=7.32. O=21.79; Found C=69.01, H=7.34, O=21.49%).

EXAMPLE 6

Preparation: Tetraisopropyl calix(4)arene tetraacetate—XVI

To 3.18 g calix(4)arene (0.0075 mole) in 85 mls dry acetone was added 6.2 g (0.045 mole) potassium carbonate anhydrous and 10.9 g (0.060 mole) isopropyl bromoacetate and the entire was refluxed under nitrogen for 6 days. The volatiles were then removed under reduced pressure and taken up into 50 mls dichloromethane which was washed well with 5% aqueous HCl, then distilled water. The organic layer was dried over dried magnesium sulphate and filtered then volatiles were removed from the filtrate to give 5.5 g (89%) off-white solid which was recrystallised from ethanol to give 3.8 g colourless crystalline product Compound XVI.

i.r. spectroscopy results $\nu$ 1750 (S) C=0 cm$^{-1}$.

EXAMPLE 7

Preparation: Tetraphenacyl p.-tert.-butylcalix(4)arene tetraacetate—XVII

Following the method of J. H. Clark and J. M. Miller in Tetrahedron Letters 7 p599 (1977) 9.4 g (0.16 mole) KF, 10.0 g (0.050mole) 2-bromoacetophenone and 11.0 g (0.0125 mole) p-t-butylcalix-4-arene tetracarboxylic acid prepared following European Patent Publication No. 0,259,016 were stirred under nitrogen in 100 mls dry HMPA at 100° C. for 17 hours. After cooling, reaction mixture was poured into ice water to give a buff coloured solid which after drying at room temperature was recrystallised from dry acetonitrile to give colourless crystalline title product Compound XVII, m.p. 97°-9° C.

Elemental Analysis calculated for $C_{84}$ $H_{88}$ $O_{16}$ C=74.55, H=6.50, O=18.93; Found C=74.34, H=6.55, H=19.11). i.r. spectroscopy $\nu$ 1703 (S) C=0 (Phenyl) 1770 (S) C=0 (O) cm$^{-1}$.

EXAMPLE 8

Preparation: Tetra tert.-butyl p-tert.-butyl dioxacalix(4)arene tetraacetate—XVIII The parent dioxacalixarene (7,13,21,27-tetra-tert-butyl-29,30,31,32-tetrahydroxy-2,3,16,17 tetrahomo-3,17-dioxacalix-4-arene) was prepared following the procedure of B. Dhawan & C. D. Gutsche, J. Org. Chem. 48 (9) p1536, 1983. To 0.5 g (0.0007 mole) parent dioxacalixarene was added 1.17 g (0.006 mole) t-butyl bromoacetate and 0.65 g (0.0047 mole) anhydrous potassium carbonate and 10 mls analar acetone and the entire was refluxed under nitrogen with stirring for 120 hours. After this time all volatiles were removed to give a sticky solid which was taken up in 20 mls dichloromethane which was then washed twice with water to give after drying of the dichloromethane layer with dried magnesium sulphate and removal of solvent 0.66 g (80%) title product which was formed as a pale yellow solid. Recrystallisation from t-butanol gave 0.5 g colourless solid title Compound XVIII mp 187°-8° C.

Elemental analysis calculated for $C_{70}$ $H_{100}$ $O_{14}$ 0.2+OH=C 71.31, H=9.20 Found C: 70.59, H=8.79; i.r. $\nu$ 1753 cm$^{-1}$ (S) C=0.

EXAMPLE 9

Preparation: Tetramethyl p-tert.-butyl dioxacalix(4)arene tetraketone—XIX

To 5.31 g (0.0074 mole) 7,13,21,27-tetra-tert-butyl-29,30,31,32-tetrahydroxy-2,3,16,17 tetrahomo-3,17-dioxacalix-4-arene prepared as in Example 8 of U.S. Pat. No. 4,855,461 Harris et. al., was added to 4.7 g (0.031 mole) sodium iodide, 4.4 g (0.032 mole) anhydrous potassium carbonate and 3.1 g (0.034 mole) chloroacetone in 150 mls anhydrous acetone and the entire was stirred under nitrogen under reflux for 17 hours. After this time all volatiles were removed and the resulting orange sticky solid was taken up in 50 mls dichloromethane which was then washed with 5% aqueous sodium thiosulphate, dried with dried magnesium sulphate and volatiles removed after filtration to give 3.4 g colourless solid product which was recrystallised from acetontrile to give 3.2 g (44% yield) colourless crystalline title product Compound XIX mp 234°-6° C. which was characterised by infra red spectroscopy and elemental analysis.

i.r. spectroscopy results $\nu$ 1718 (S) cm$^{-1}$ C=0; Elemental Analysis (calculated for $C_{58}$ $H_{76}$ $O_{10}$. $CH_3$ CN C=73.97, H=8.17; Found C=74.47, H=8.42)

EXAMPLE 10

Preparation: Tetra methoxyethyl p.tert.butyldioxacalix(4)arene tetraacetate—XX 1.6 g (0.0015 mole) tetraethyl acetate of 7,13,21,27-tert-butyl-29,30,31,32-tetrahydroxy-2,3,16,17-tetrahomo-3,17-dioxacalix-4-arene (Compound 61) prepared following U.S. Pat. No. 4,855,461 Harris et. al., was refluxed for 72 hours under nitrogen with stirring with 5 mls methoxyethanol and a crystal of p-toluenesulphonic acid as transesterfication catalyst. After removal of about half of the methoxyethanol under reduced pressure high purity crystalline product crystallised out as colourless crystals. Yield 0.7 g (39% yield) of title product Compound XX, mp 178°-82° C., which was characterised by infra red spectroscopy and elemental analysis.

i.r. Spectroscopy results $\nu$ 1760 (S) cm$^{-1}$ C=0. Elemental Analaysis (calculated for $C_{66}$ $H_{92}$ $O_{18}$. C=67.56, H=7.90; Found C=70.04, H=8.30).

EXAMPLE 11

Preparation: Tetraethylthio p-tert.butyloxacalix(4)arene tetraacetate—XXI

To 0.43 g (0.00042 mole) tetra-ethyl acetate of 7,13,19,25-tetra tert.butyl-27,28,29,30-tetrahydroxy-2,3-dihomo 3-oxacalix(4)arene (Compound 60) prepared following U.S. Pat. No. 4,855,461 S. Harris et. al., was added 2.1 g (0.037 mole) potassium hydroxide and 4 mls ethanol and 4 mls water and the entire was refluxed for 17 hours. After the reaction mixture had cooled down it was added to 10% aqueous HCl and the resulting white precipitate washed with a little water and dried to give 0.36 g (92% yield) mono-oxacalix-4-arene tetracarboxylic acid which was added to 2 mls thionyl chloride and refluxed under nitrogen with stirring 3 hours to give after removal of all volatiles 0.4 g (100%) oxacalix-4-arene tetracarboxylic acid chloride. The acid chloride was dissolved in 5 mls dry THF and to a stirred reaction mixture under $N_2$ at 0° C. was added 0.27 g (0.0034 mole) pyridine and 0.21 g ethane thiol. An off-white solid formed and the reaction mixture was stirred under N₂ for a further 17 hours at room temperature, then all volatiles were removed to give 0.5 g solid product which was taken up in 10 mls dichloromethane which was washed well with water and dried over dried magnesium sulphate to give after removal of volatiles 0.46 g (98%) product which was chromatographed on neutral alumina with dichloromethane as diluent to give high purity Compound XXI as a heavy colourless oil.

i.r. spectroscopy $\nu$ (S) 1680 (S) C=0 cm⁻¹.

EXAMPLE 12

Preparation: Tetraethylthio p.tert.butyldioxacalix(4)arene tetraacetate—XXII

Dioxacalix(4)arene tetracarboxylic acid chloride was prepared by the same procedure as for the mono-oxacalix(4)arene derivative in Example 11, starting from the tetraethyl acetate used as starting material in Example 10. To 1.75 g of the acid chloride in 10 mls dry THF under nitrogen with stirring at 0° C. was added 0.84 g (0.0136 mole) ethane thiol and 1.07 g (0.0136 mole) pyridine dropwise. An off-white precipitate formed. The reaction mixture was allowed to warm to room temperature and stirred a further 17 hours under nitrogen at room temperature. After this time all volatiles were removed, the residue was taken up in 15 mls dichloromethane which was washed well twice with water then dried over dried magnesium sulphate. Removal of volatiles under reduced pressure gave 1.7 g (95% yield) which was recrystallised from ethanol to give colourless crystalline product Compound XXII, mp 186°-90° C.

i.r. spectroscopy results $\nu$ 1677 (S) C=0 (S) cm⁻¹. Elemental Analysis (calculated for $C_{62}$ $H_{84}$ $O_{10}$ $S_4$: C=66.63 H=7.58 Found C=66.89 H=7.60%).

EXAMPLE 13

Preparation: Tetra (-2-pyridinio-)ethyl p-tert.butylcalix(4)arene tetraacetate—XXIII To 3.1 g of p-t-butylcalix(4)arene tetra acetyl chloride (0.0032 mole) in 20 mls NaH dried THF (tetrahydrofuran) at 0° C. was added dropwise with stirring during 15 minutes 2.04 g (0.026 mole) dry pyridine and 3.2 g (0.026 mole) 2-pyridine ethanol under nitrogen. A white precipitate formed and the reaction mixture was then allowed to stir at room temperature for 72 hours. The reaction mixture was then poured into 100 mls ice water and then extracted with dichloromethane which was washed well twice with water, then dried over magnesium sulphate to give after removal of volatiles an off-white waxy solid 2.8 g mp 88°-90° C. elution with dichloromethane through neutral alumina provided title tetraester Compound XXIII as a colourless solid, mp 90°-1° C.

i.r. spectroscopy results $\nu$ 1750 (S) cm⁻¹ C=0. Elemental Analysis results: (calculated for $C_{80}$ $H_{92}$ $O_{12}$ $N_4$: C=73.82, H=7.12, O=14.75; N=4.30; Found C=73.28, H=7.08, O=14.61, N=4.18).

EXAMPLE 14

Preparation: Heptaethyl p-ethylcalix(7)arene heptaacetate—XXIV p-Ethylcalix-7-arene was prepared following the method of Z. Asfari and J. Vicens Makromol Chem. Rapid Commun. 10 p181, 1989 and 1.34 g (0.0014 mole) of same was added to 3.34 g (0.02 mole) ethyl bromoacetate and 2.08 g (0.015 mole) anhydrous potassium carbonate and 20 mls. dry analar acetone and the entire was refluxed with stirring under nitrogen for 120 hours. After this time all volatiles were removed, the last traces under reduced pressure, and the residual heavy pale brown oil that remained added to 20 mls. dichloromethane and 20 mls. 5% aqueous $H_2SO_4$. After shaking the two layers together the organic layer was separated off then washed with water and dried with dried magnesium sulphate and dichloromethane removed, the last traces under reduced pressure, to give 1.8 g (82%) pale yellow oil which was chromatographed on basic alumina using dichloromethane as eluent to give a colourless oil product Compound XXIV which solidified on standing after removal of dichloromethane, mp 46°-7° C.

i.r. analysis $\nu$ 1750 cm⁻¹(s) C=0. Elemental Analysis Calculated for $C_{91}$ $H_{112}$ $O_{21}$ C=70.89, H=7.32, Found C=70.99, H=7.48%.

EXAMPLE 15

Preparation: Octamethoxyethyl p.-tert.-butylcalix(8)arene octaacetate—XXV 2.4 g (0.0012 mole) of the octaethylacetate of p-t-butyl calix(8)arene was prepared following the procedure of U.S. Pat. No. 4,556,700 Harris et. al., (also JACS III, 23 1989 p8681), then to this was added 10 g methoxyethanol and a crystal of p-toluene sulphonic acid as catalyst. The entire was refluxed under $N_2$ for 48 hours following which all volatiles were removed the last traces under reduced pressure to give 2.7 g (100% yield) product which was recrystallised from ethanol to give high purity title product Compound XXV mp 193°-4° C.

Elemental Analysis Calculated for $C_{128}$ $H_{176}$ $O_{32}$ C=69.06, H=7.91, O=23.07, Found C=68.23, H=7.97, O=22.21.

EXAMPLE 16

Preparation: Tetra methoxyethyl p-tert.butyloxacalix(4)arene tetraacetate—XXVI

To 2.0 g of the tetraethylacetate of 7,13,19,25-tetra-tert. butyl-27,28,29,30-tetrahydroxy-2,3-dihomo-3-oxacalix(4)arene prepared following U.S. Pat. No. 4,855,461 by S. Harris of Loctite (Ireland) Limited was added 9 g methoxyethanol and a crystal of p-toluene sulphonic acid and the entire was refluxed under nitrogen for 48 hours following which all volatiles were removed, the last traces under reduced pressure, to give 2.2 g (100%) of colourless oil product Compound XXVI.

i.r. analysis $\nu$ 1748 (S) C=0. Elemental Analaysis Calculated for $C_{65}$ $H_{94}$ $O_{17}$ C=68.04, H=8.26, O=23.71 Found C=67.16, H=8.11, O=22.90.

EXAMPLE 17

Preparation: Tetra tert.-butyl p-tert.butyloxacalix(4)arene tetraacetate—XXVII

This compound was prepared following the procedure of U.S. Pat. No. 4,855,461 by S. Harris of Loctite (Ireland) Limited for the ethyl acetate product substituting t-butyl bromoacetate for ethyl bromoacetate; mp 125°-8° C.

i.r. $\nu$ 1745 (S) C=0. Elemental Analysis Calculated for $C_{69}$ $H_{98}$ $O_{13}$ C=70.98, H=8.46; Found C=70.49, H=8.86.

EXAMPLE 18

Preparation: Hexaethylthio p.tert.butylcalix(6)arene hexaacetate—XXIX 2.4 g (0.0016 mole) of the hexaethyl acetate of p-t-butyl calix(6)arene was prepared following procedure of U.S. Pat. No. 4,556,700 Harris et. al., (also JACS III, 23 1989 p8681) and to this was added 7.4 g (0.132 mole) potassium hydroxide and 15 mls ethanol and 15 mls water and the entire was refluxed for 17 hours. After this time the cooled reaction mixture was poured in excess 10% aqueous HCl and the white precipitate washed with water and dried to give 2.1 g 98% hexa acid whose structure was confirmed by i.r. spectroscopy.

The acid was added to 10 mls. thionylchloride and the entire was refluxed under nitrogen for 2.5 hours following which all volatiles were removed to give the hexa acid chloride which was not purified further in view of its moisture sensitivity i.r. $v$ 1800 cm$^{-1}$ (S) C=0. Twenty mls. dry THF was added to the acid chloride to give a clear solution following which was added 0.9 g (0.014 mole) ethyl mercaptan and 1.5 g (0.019 mole) pyridine under nitrogen at 0° C. After warming to room temperature the reaction mixture was stirred a further 17 hours at room temperature following which all volatiles were removed and the residue was taken up in dichloromethane which was washed well with water then dried over dried magnesium sulphate to give colourless solid title product Compound XXIX 2.4 g (94%) which was recrystallised from methanol/dichloromethane to give colourless crystals, mp 241°-2° C.

i.r. $v$ 1680 (S) C=0 (S) cm$^{-1}$. Elemental Analysis Calculated for $C_{90}H_{120}O_{12}S_6$: C=67.91, H=7.89; Found C=68.14, H=7.32%.

EXAMPLE 19

Preparation: Hexamethoxyethyl p.tert.butylcalix(6)arene hexaacetate—XXX 2.4 g (0.0016 mole) of the hexaethyl acetate of p-t-butylcalix(6)arene was prepared following the procedure of U.S. Pat. No. 4,556,700 Harris et. al., (also JACS III, 23 1989 p8681), then to this was added 10 g methoxyethanol and a crystal of p-toluene sulphonic acid catalyst. The entire was refluxed under N$_2$ for 48 hours following which all volatiles were removed the last traces under reduced pressure to give 2.7 g (100%) solid product which was recrystallised from ethanol to give pure title product Compound XXX mp 157°-8° C.

Elemental Analysis Calculated for $C_{96}H_{132}O_{24}$ C=69.06, H=7.91, O=23.07; Found C=68.68, H=7.96, O=21.84.

EXAMPLE 20

Preparation: Hexa tert.-butyl p.tert.butylcalix(6)arene tetraketone—XXXI 8.1 g (0.0083 mole) p-t-butylcalix-6-arene and 10.4 g (0.075 mole) anhydrous potassium carbonate, 8.3 g (0.052 mole) dried potassium iodide 10.8 g (0.060 mole) 1-bromopinacolone and 200 mls. dry analar acetone were refluxed with stirring under nitrogen for 24 hours. After this time all volatiles were removed from the reaction mixture and the yellow solid residue was added to 3% aqueous sulphonic acid (1l) and a pale yellow precipitate obtained on filtration was extracted into 100 mls. dichloromethane which was washed twice with water dried over dried magnesium sulphate filtered and the solvent removed from the filtrate to give 8.5 g colourless crude title product which was stirred with 25 mls. dry analar acetone. The colourless solid that was filtered off 1.6 g was confirmed to be high purity product Compound XXXI by HPLC analysis mp above 230° C.

i.r. analysis $v$ 1720 (S) C=0. HPLC Analysis one main product 99.0% 7.90 minutes. HPLC Analysis was conducted with a Waters Associates Model 440 and Radpak C18 reverse phase column UV detector Pye Unicam PV 4020 set at $\lambda$ m 280 nm 1.5 ml/minute (20% water, 80% THF) isocratic.

EXAMPLE 21

Preparation: p-t-Butylcalix(8)arene octa-t-butyl ketone—XXXII

A mixture of p-t-butylcalix(8)arene (16.20 g, 0.03 mol), potassium carbonate (20.70 g, 0.15 mol), 1-bromopinacolone (21.50 g, 0.12 mol), potassium iodide (16.60 g, 0.10 mol) and acetone (200 ml) was refluxed with stirring under a N$_2$ atmosphere for 72 hours. After cooling, the reaction mixture was filtered and the filtrate was added to 3% aqueous sulphuric acid (2 ) and the off-white precipitate obtained on filtration was extracted into dichloromethane (200 ml). The organic layer was washed twice with water dried over MgSO$_4$, filtered and the solvent evaporated to give a yellow solid (24.40 g). Recrystallisation from ethanol gave 23.20 g (89.00% yield) of the colourless crystalline ketone Compound XXXII, m.p. 258°-261° C.

Elemental Analysis: (Found C, 78.53; H, 9.51. Calculated for $C_{136}H_{192}O_{16}$ C, 78.48; H. 9.22) IR (KBr) $v_{max}$ 1720 cm$^{-1}$ (C=0 ketone); HPLC analysis was conducted with a Waters Associates Model 440 and micro Bondapak C18 reverse phase column, uv detector Pye Unicam PV 4020 set at $\lambda_m$ 280 nm, 1.5 ml/minutes (20% water, 80% THF) isocratic, one main product (97%), 10.0 minutes.

EXAMPLE 22

Preparation: Tetra(-1-pyrolidin-2-onyl)ethyl p-tert.butylcalix(4)arene tetraacetate—XXXIII To 3.1 g of p-t-butylcalix(4)arene acetyl chloride (0.0032 mole) in 20 mls. NaH dried THF (tetrahydrofuran) at 0° C. was added dropwise with stirring during 15 minutes 2.04 g (0.026 mole) dry pyridine and 3.36 g (0.026 mole) 1-(2-hydroxyethyl)-2-pyrolidinone under nitrogen. A white precipitate formed and the reaction mixture was then allowed to stir at room temperature for 72 hours. The reaction mixture was then poured into 100 mls ice-water and the off-white precipitate was filtered off and then taken up in 50 mls. dichloromethane which was washed well twice with water then dried over magnesium sulphate to give after removal of volatiles an off white solid 2.9 g.

Eliction with dichloromethane through neutral alumina provided title tetraester Compound XXXIII, a colourless solid mp 126°-134° C.

i.r. spectroscopy results $v$ 1750 (S) cm$^{-1}$ C=0. Elemental analysis results: (Calculated for $C_{76}H_{100}O_{16}N_4$ C=68.86, H=7.60, N=4.23; Found C=67.76, H=7.69, N=3.82%.

EXAMPLE 23

Preparation: Tetramethoxyethyl calix(4)arene tetraacetate (partial cone)—XXXIV 1.3 g partial cone Compound XVa prepared in Example 5 was refluxed 72 hours in 10 g methoxyethanol and a small crystal of p-toluene sulphonic acid under dry nitrogen. After this time all volatiles were removed under reduced pressure to give title product Compound XXXIV as 1.3 g pale yellow very heavy oil.

i.r. analysis $\nu$ 1760 cm$^{-1}$ (S) C=O. Elemental Analysis Calculated for $C_{76} H_{100} O_{16}$ C=64.85, H=6.35; Found C=63.13, H=6.28%).

Compounds prepared as in J. Am. Chem. Soc. 111, 23, 1989, p8681 and U.S. Pat. No. 4,866,198 Harris:

| No. | |
|---|---|
| 35 | Tetraethyl p-tert.-butylcalix(4)arene tetraacetate |
| 36 | Tetramethyl p-tert.-butylcalix(4)arene tetraacetate |
| 37 | Tetraethyl calix(4)arene tetraacetate |
| 38 | Tetramethyl calix(4)arene tetraacetate |
| 39 | Tetraphenyl p-tert.-butylcalix(4)arene tetraacetate |
| 40 | Hexamethyl calix(6)arene hexaacetate |
| 41 | Hexaethyl calix(6)arene hexaacetate |
| 42 | Hexaethyl p-tert.-butylcalix(6)arene hexaacetate |
| 43 | Tetraphenyl p-tert.-butylcalix(4)arene tetraketone |
| 44 | Tetra tert.-butyl p-tert.-butylcalix(4)arene tetracetate |
| 45 | Tetra tert.-butyl p-tert.-butylcalix(4)arene tetraketone |
| 46 | Tetramethyl p-tert.-butylcalix(4)arene tetraketone |
| 47 | Tetra-1-adamantyl p-tert.-butyl calix(4)arene tetraketone |
| 59 | Tetrabenzyl p-tert.-butylcalix(4)arene tetraacetate |

Preparation of oxime Compound 50 according to Irish Patent Application No. 3982/89 of Loctite (Ireland) Limited

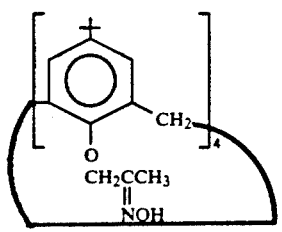

0.5 g tetramethyl p-tert.-butylcalix(4)arene tetraketone prepared as in European Patent Publication No. 0.262,910 (Application No. 87 308 585/6) was refluxed with 0.5 g hydroxylamine hydrochloride, 5 ml absolute ethanol and 0.5 ml pyridine following the procedure described in Vogel's Textbook of Practical Organic Chemistry, 4th Edition, B. S. Furniss, Longman N.Y. 1981, p1112 for 2 hours, following which all volatiles were removed and the residual solid washed well with water to give 0.5 g (94%) product which was recrystallised from ethanol-water to give pure colourless crystalline product, mp 138°-9° C., characterised as title compound 50 by i.r. spectroscopy and elemental analysis.

i.r. spectroscopy results: no peak at 1720 cm$^{-1}$ from starting material 3250 cm$^{-1}$(m) NOH. Elemental Analysis results: (Calculated for Compound XIV.CH$_3$ CH$_2$ OH: $C_{58} H_{82} N_4 O_9$ C=71.13, H=8.44, N=5.72, O=14.70; Found C=68.54, H=8.08, N=5.31, O=14.37).

Preparation of methacrylated Compound 53 according to Irish Patent Application No. 3986/89 of Loctite (Ireland) Limited a.

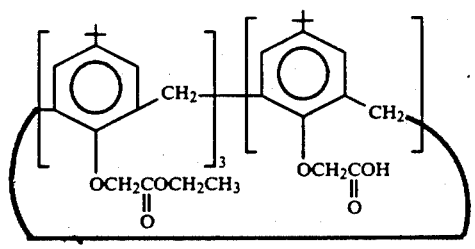

To 5.01 g (0.005 mole) of the tetraethylacetate of p-t-butylcalix-4-arene prepared by the method described in U.S. Pat. No. 4,556,700 Harris et. al., in 100 mls chloroform was added 20 drops (0.2 ml) (0.0026 mole) trifluoroacetic acid and the solution was stirred at room temperature for 22 hours. After this time the chloroform solution was washed well with water, then the organic phase was dried over dried magnesium sulphate. The volatiles were removed to give 4.9 g (100% yield) of colourless crude product. Recrystallisation from aqueous ethanol gave 4.3 g (88%) colourless crystalline title compound of formula 51; m.p. 166°-9° C.

i.r. spectroscopy results $\nu$ 3510 (W) 3360 (W) OH, 1750(S) C=O. Elemental analysis results: (calculated for $C_{58} H_{76} O_{12}$ C:72.22, H 7.88; Found: C 72.29, H 7.71)

b. Preparation

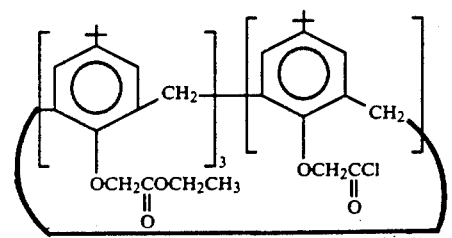

To 4.15 g (0.0044 mole) of the monoacid 51 was added 10 mls thionyl chloride under nitrogen with stirring. The reaction mixture was then refluxed for 2 hours, following which excess thionyl chloride was distilled off under nitrogen and the last traces at reduced pressure to give 4.3 g acid chloride title compound of formula 52 as an off white solid which was not further purified in view of its moisture sensitivity.

c. Preparation

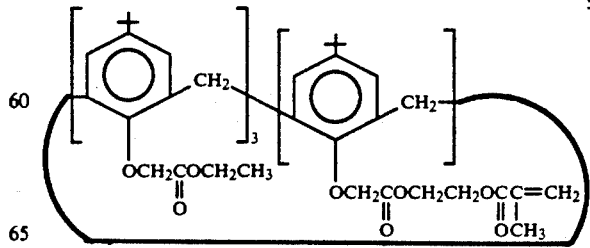

To 4.3 g (0.0044 mole) of the acid chloride 52 in 20 mls NaH dried THF was added dropwise with stirring under nitrogen 1.71 g (0.013 mole) 2-hydroxyethyl methacrylate, 5 mg naphthoquinone free radical stabiliser and 1.5 g (0.015 mole) triethylamine. The reaction mixture was cooled with a cool air drying gun during addition as the reaction was exothermic and a white precipitate formed. The reaction mixture was then allowed to stir at room temperature for a further 17 hours following which all volatiles were removed, the last traces at reduced pressure, and the reaction mixture was then added to the water to give an off-white solid precipitate which was filtered off, then taken up in 100 mls dichloromethane which was washed well with water and dried with dried magnesium sulphate to give after removal of volatiles 4.5 g of off-white product. Chromatography on neutral alumina using dichloromethane as eluent gave high purity title product of formula 53 as a colourless solid; m.p. 63°-5°.

i.r. spectroscopy results: $\nu$ 1760(S) C=O(CH$_2$), 1722(S) C=O (C-CH$_3$), 1630(W) C=C.

Elemental analysis results: (Calculated for C$_{64}$ H$_{84}$ O$_{14}$ C:71.35, H:7.86, O:20.79; Found C:71.00, H:7.55, O:20.82).

Preparation Linear Polymer

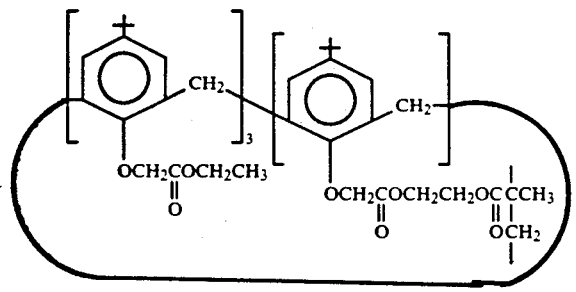

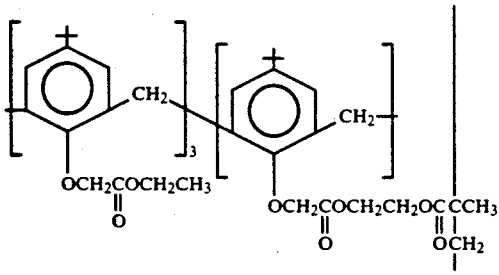

0.7 g of the compound 53 was dissolved in 2 g toluene containing 20 mg AZBN (azoisobutyronitrile) and the resulting solution was stirred in a round bottom flask with reflux condenser on it for 17 hours immersed in an oil bath at 87° C. After this period of time the cooled reaction mixture was poured into a large volume of methanol to give a fine white solid which was washed well with more methanol to give 0.37 g linear polymer which was soluble in common organic solvents such as dichloromethane, acetone and THF.

i.r. spectroscopy results: no C=C at 1630 cm$^{-1}$; HPLC analysis: Waters Millipore Sugar Analyser/liquid chromatograph; Ultrastyragel THF linear mix bed column; THF as eluent, 1.0 mls/min. R1 Detector retention volume 9.8 minutes; m.w. 6745 (mp).

Preparation of Tetramethacrylated Compound

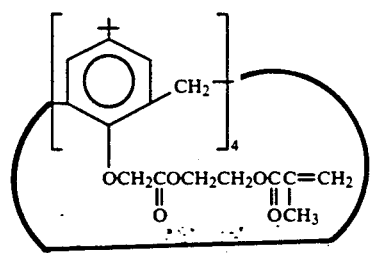

To 10.4 g (0.011 mole) p-t-butyl calix(4)aryl tetracecetyl chloride prepared as described in European Patent Publication No. 0,259,016 (Application No. 87 306 963.7) in 100 mls NaH dried THF under nitrogen with stirring was added 11.8 g (0.091 mole) 2-hydroxyethyl methacrylate, 10 mg napththoquinone, and 9.3 g (0.091 mole) triethylamine dropwise with stirring while cooling with a cool air gun. A white precipitate formed. The reaction mixture was then stirred for a further 17 hours at room temperature after which volatiles were removed, the last traces at reduced pressure. The solid was then added to ice water and the off-white precipitate product taken up in 250 mls dichloromethane which was washed well with water, then dried with dried magnesium sulphate to give after removal of volatiles 12.9 g pale yellow oil product which solidified on standing. Chromatography on neutral alumina using dichloromethane gave high purity colourless solid title product of formula 55; m.p. 42°-5° C.

i.r. spectroscopy results: $\nu$ 1760(S) C=O(CH$_2$), 1720(S) C=O (C-CH$_3$) 1633(m) C=C.

Elemental analysis results: (Calculated for C$_{76}$ H$_{96}$ O$_{20}$. C=68.65, H=7.28, O=24.07; Found C:68.25, H 7.36, O=24.10).

Preparation of Hexaethyl p-allylcalix(6)arene hexaacetate—Compound 59 a. Preparation: 37,38,39,40,41,42-Hexahydroxycalix-(6)arene.

Compound 56:

A mixture of p-t-butylcalix(6)arene (7.92 g, 8.14 mmol) and finely ground aluminium trichloride (13.04 g, 0.10 mol) in toluene (150 ml) was stirred at room temperature under a N$_2$ atmosphere for 27 hours. Then dilute sulphuric acid and water were added to destroy the excess Lewis acid and toluene was removed at reduced pressure. The crude residue was extracted into dichloromethane and the organic layer was washed with dilute sulphuric acid and water, dried over MgSO$_4$, filtered and the solvent evaporated to give an orange coloured oily residue. On addition of ether precipitation occurred. The crude solid product was recovered by filtration, giving 4.02 g of an orange solid. Flash column chromatography on the impure solid (eluent: hexane/dichloromethane 1:1), yielded 3.20 g (62% yield) of white solid product, Compound 56. m.p. >250° C. (decomp.)

Found: C, 79.11; H, 5.74. Calc. for C$_{42}$ H$_{36}$ O$_6$: C, 79.26; H, 5.66). IR (KBr) $\nu_{max}$ 3245 cm$^{-1}$ (OH);

b. Preparation: 37,38,39,40,41,42-Hexakis(allyloxy)-calix(6)arene.

Compound 57: (a) To sodium hydride (50% dispersion in oil, pre-washed with hexane) (2.00 g, 0.08 mol) in tetrahydrofuran (100 ml) was added calix(6)arene (Compound 56) (1.00 g, 1.57 mmol). The mixture was heated to reflux and then allyl bromide (10 ml, 0.12 mol) was added dropwise to the refluxing mixture. The reaction was maintained at reflux with stirring for 48 hours under a $N_2$ atmosphere. On cooling, excess sodium hydride was destroyed by cautious addition of ethanol. Solvents were evaporated to give a white solid residue, which was taken up in a $CH_2Cl_2/H_2O$ mixture and transferred to a separating funnel, where the organic layer was separated and washed with water, dried over $MgSO_4$, filtered and the solvent evaporated to give a white solid (1.13 g). Column chromatography on 0.61 g of product (eluent: hexane/dichloromethane 1:3), yielded 0.43 g of pure product Compound 57. Recrystallisation from $CH_2Cl_2/CH_3CH_2OH$ gave 0.38 g (50% yield) of white solid, m.p. >268° C. (decomp.).

(Found: C, 82.05; H, 7.04. Calc. for $C_{60}H_{60}O_6$: C, 82.19; H, 6.85). IR (KBr) $\nu_{max}$1645 cm$^{-1}$ (C=C, vinyl);

c. Preparation: 5,11,17,23,29,35-Hexa-p-allyl-37,38,39,40,41,42-hexahydroxycalix(6)arene.

Compound 58:

A Claisen Rearrangement was effected by taking hexaallyloxycalix(6)arene (Compound 57) (1.96 g, 2.24 mmol) in diethylaniline (40 ml) and refluxing the mixture with stirring under a $N_2$ atmosphere for 4 hours. The cooled reaction mixture was poured onto a mixture of 50 ml ice-water and 50 ml conc. HCl and the precipitate was recovered by filtration. Remaining traces of the solvent were removed by taking the product in dichloromethane and shaking with a 10% hydrochloric acid solution. The organic layer was then washed with water, dried over $MgSO_4$, filtered and the solvent evaporated to give 1.66 g of a dark brown solid residue. Flash column chromatography (eluent: hexane/dichloromethane 1:1), gave a pale yellow solid (0.70 g) and recrystallisation from $CH_2Cl_2/(CH_3)_2CHOH$ gave 0.31 g (15% yield) of white solid Compound 58, m.p. >300° C.

(Found: C, 82.51; H, 7.13. Calc. for $C_{60}H_{60}O_6$: C, 82.19; H, 6.85). IR (KBr) $\nu_{max}$3245 cm$^{-1}$ (OH), 1640 cm$^{-1}$ (C=C, vinyl).

Preparation: (Hexaethyl p-allylcalix(6)arene hexaacetate).

Compound 62:

A mixture of p-allylcalix(6)arene (Compound 58) (1.01 g, 1.15 mmol), potassium carbonate (1.93 g, 0.01 mol) and ethyl bromoacetate (1.60 ml, 0.01 mol) in acetone (150 ml) were refluxed with stirring for 5 days (with a silica gel drying tube in place to keep out external moisture). On cooling, excess salts were removed by filtration. Evaporation of the solvent yielded a yellow oil which solidified on addition of ethanol. The solid product was recovered by filtration and was taken up in a hot solution of $CH_2Cl_2/CH_3CH_2OH$. On cooling, crystallisation occurred and after filtration a yellow crystalline solid (1.35 g) was obtained. Recrystallisation from $CH_2Cl_2/CH_3CH_2OH$ gave 1.23 g (77% yield) of a white crystalline solid, showing a single spot on t.l.c., $R_f$ 0.65, (eluent: hexane/dichloromethane/methanol 30:30:2), m.p. 154°-159° C.

(Found: C, 72.16; H, 6.91. Required for $C_{84}H_{96}O_{18}$: C, 72.41; H, 6.90). IR (KBr) $\nu_{max}$1750, 1730 cm$^{-1}$ (C=O, acetate), 1635 cm$^{-1}$ (C=C, vinyl).

(c) Electrode Fabrication and Measurements

PVC membrane electrodes were fabricated as described in Analyst, September 1990, Vol. 115, 1207.

The calixarene and oxacalixarene derivatives as discussed above were each used as ligand in a membrane composition.

The membrane components: PVC, potassium tetrakis (p-chlorophenyl)borate (KTpClPB), 2-nitrophenyl octyl ether (2-NPOE) and Selectophore grade tetrahydrofuran (THF) were obtained from Fluka; AnalaR grade chlorides of caesium, sodium, potassium, lithium, rubidium, magnesium, calcium and ammonium were supplied by Riedel-de-Haen and dissolved in distilled, de-ionised water.

The general procedure for the preparation of the polymeric membrane was as follows: PVC, 180 mg; ligand, 2 mg; plasticiser 2-NPOE, 360 mg; and KTpClPB, 0.5 mg (except where specified) were dissolved in THF. The solution was then poured into a 30 mm square glass mould and covered to prevent particle contamination in a manner similar to that described by Moody and Thomas in Edmonds "Chemical Sensors", Blackie, Chapman, and Hall, New York, 1988, p.75-77. Gradual evaporation at room temperature gave a transparent flexible membrane of about 0.1 mm in thickness. A 9-mm diameter disc was then removed with a cork borer and inserted into the cap of a Russell Model ISE 97-7809 gas sensing electrode (the diameter of the exposed membrane was 7 mm). The electrode design enables the PVC discs to be conveniently clipped on to the electrode tip, rather than being glued.

Coated electrodes were conditioned by immersion in $10^{-1}$M chloride salt solution of the target (or primary) cation for at least 30 minutes prior to use. The internal reference electrolyte was $10^{-1}$M chloride salt of the target cation. Electrochemical measurements were made relative to a saturated calomel reference electrode (SCE) using a Philips PW 9421 digital pH/millivolt meter coupled to a Philips PM8251 single-pen recorder. The SCE was a Metrohm capillary tip (Ref. 6.0705.000) chosen for its stability and very low rate of KCl leakage. The selectivity coefficients (Log $K_{i,j}^{pot}$) were determined by the separate solution method using $10^{-1}$M chloride solutions of the cations listed in the tables below and the Group II cation and hydrogen ion selectivities were confirmed by the mixed solution (fixed interference) method using background fixed concentrations of $1 \times 10^{-1}$ and $1 \times 10^{-2}$M solutions of the interfering ion while varying the concentration of the target ion over the range $10^{-6}$–$10^{-1}$M. Further details regarding the methodology can be obtained from "Selective Ion—Sensitive Electrodes" by J. G. Moody and J. D. R. Thomas, Merrow, Watford, 1971.

$K_{i,j}^{pot}$ is the selectivity coefficient or a weighting which takes account of the relative contribution of an interfering species j to the total emf of the cell. Selectivity coefficient measurements are on a logarithmic scale. A value of less than $-2$ for any listed cation indicates a remarkably high level of selectivity (over $10^2$ times more selective) of the target cation over that listed cation. For example in the table below for sodium-ion selective electrodes, Compound XII is several hundred times more selective for Na$^+$ than for any of the listed cations, and is $10^4$ times more selective for Na$^+$ than for Ca$^{2+}$ or Mg$^{2+}$. The selectivity coefficients set out in the following tables were not predictable from known results.

Relevance of Slope

The slope of an electrode targeted at monovalent cations in theory should be 59.2 mV per decade change in ion activity at 25° C. (Nernstian slope). In practice, sub-Nernstian slopes are common and a slope of over 50 mV per decade is usually satisfactory.

Selectivity coefficients for Sodium-selective electrodes

| Compound No. | $R^3$ | $R^2$ | Slope mv/decade | $K^+$ | $Li^+$ | $Cs^+$ | $Rb^+$ | $H^+$ | $Ca^{2+}$ | $Mg^{2+}$ | $NH_4^+$ |
|---|---|---|---|---|---|---|---|---|---|---|---|

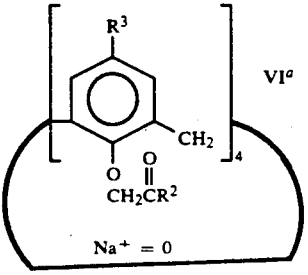

VI[a]

$Na^+ = 0$

| Compound No. | $R^3$ | $R^2$ | Slope mv/decade | $K^+$ | $Li^+$ | $Cs^+$ | $Rb^+$ | $H^+$ | $Ca^{2+}$ | $Mg^{2+}$ | $NH_4^+$ |
|---|---|---|---|---|---|---|---|---|---|---|---|
|  | t-Bu | On-Bu | 53.50 | −2.2 | −2.2 | −2.8 | −3.0 | −2.0 | −1.7 | −1.6 | — |
| 44 | t-Bu | Ot-Bu |  | −1.4 | −2.1 | −2.9 | −0.2 | −2.3 | −3.4 | −5.4 | −2.7 |
| 36 | t-Bu | $OCH_3$ | 60 | −2.5 | −2.9 | −1.6 | −3.1 | −2.0 | — | — | — |
| 59 | t-Bu | $OCH_2C_6H_5$ |  | −1.5 | −2.5 | −2.1 | −2.0 | −1.0 | −2.0 | −3.4 | −0.8 |
| XII | t-Bu | $OCH_2CH_2OCH_3$ | 53.60 | −2.5 | −3.8 | −3.4 | −2.6 | −2.8 | −4.3 | −4.3 | −2.8 |
| 55 | t-Bu | $OCH_2CH_2OCC=CH_2$ with $OCH_3$ | 43.70 | −1.5 | −2.8 | −2.3 | −2.4 | −2.7 | −3.1 | −3.2 | −3.1 |
| XI | t-Bu | $OCH_2CH_2OEt$ |  | −1.4 | — | — | — | — | — | — | — |
| XIII | t-Bu | $OCH_2CH_2On-Bu$ |  | −1.0 | — | — | — | — | — | — | — |
| 35 | t-Bu | OEt | 60 | −1.9 | −2.5 | −1.6 | — |  | −2.5 | >−6 |  |
| 38 | H | $OCH_3$ | 60 | −2.6 | −4.1 | −3.6 | −4.0 | −4.6 | −4.2 | −3.9 | −2.9 |
| XVI | H | $OCH(CH_3)_2$ |  | +0.1 | −1.6 | 0.6 | 0.9 | −1.0 | −3.2 | −2.3 | −0.4 |
| XV[b] | H | Ot-Bu (Cone) |  | 0.0 | −1.0 | −0.5 | −1.5 | −1.8 | −1.8 | −1.8 | −2.0 |
| XIV | H | $OCH_2C_6H_5$ |  | 0 | −5.6 | −2.0 | −2.8 | −2.0 | −6.0 | −5.0 | −3.2 |
| XVII | t-Bu | $OCH_2C(O)C_6H_5$ |  | −2.1 | −2.3 | −2.2 | −2.6 | −0.6 | −2.7 | −1.4 | −2.8 |
| 39 | t-Bu | $OC_6H_5$ | 45.60 | −1.5 | −2.5 | −1.2 | −1.4 | −1.2 | −3.0 | −3.3 | −2.4 |
| 45 | t-Bu | t-Bu | 64 | −1.1 | −1.7 | −2.3 | — | — | −2.8 | −2.3 | — |
| 46 | t-Bu | $CH_3$ | 57 | −2.3 | −2.5 | −2.7 | — | — | −2.6 | −2.3 | — |
| 47 | t-Bu | Adamantyl | 53.3 | −0.1 | −0.7 | −1.6 |  |  | −1.0 | −1.9 | — |
| 43 | t-Bu | $C_6H_5$ | 56.20 | −2.3 | −2.7 | −3.9 | −3.7 | −3.1 | −3.3 | −4.2 | −3.5 |
| XXIII | t-Bu | $OCH_2CH_2$-pyridyl | 42.5 | −2.0 | −2.3 | −1.1 | −2.5 | −1.5 | −3.1 | −3.9 | −3.1 |
| XXXIII | t-Bu | $OCH_2CH_2N$-pyrrolidinonyl | 40.7 | −2.1 | −2.9 | −1.5 | −2.9 | −1.6 | −3.4 | −4.0 | −3.1 |
| 53 |  |  | 55.10 | −1.3 | −3.1 | −3.1 | −3.4 | −4.1 | −4.9 | −5.3 | −2.9 |
| Linear Polymer of Compound 53 |
| 54 |  |  | 54.90 | −0.9 | −2.4 | −1.2 | −1.4 | −2.2 | −3.0 | −2.8 | −1.8 |

-continued

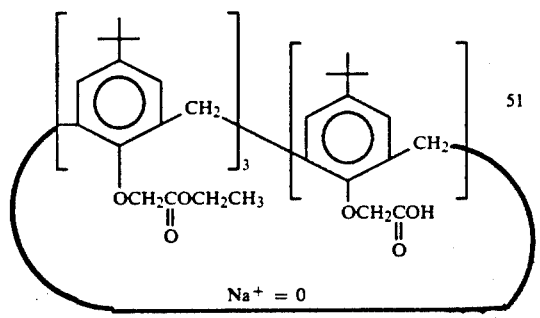

| | | | | | | | | | |
|---|---|---|---|---|---|---|---|---|---|
| 51 | | | 53.0 | −2.4 | −3.1 | — | — | −1.9 | −3.5 | −3.3 | −3.3 |

Selectivity for Potassium-Selective electrodes

| Compound No. | R³ | R² | Slope | Na⁺ | Li⁺ | Cs⁺ | Rb⁺ | NH₄⁺ | H⁺ | Ca²⁺ | Mg²⁺ |
|---|---|---|---|---|---|---|---|---|---|---|---|

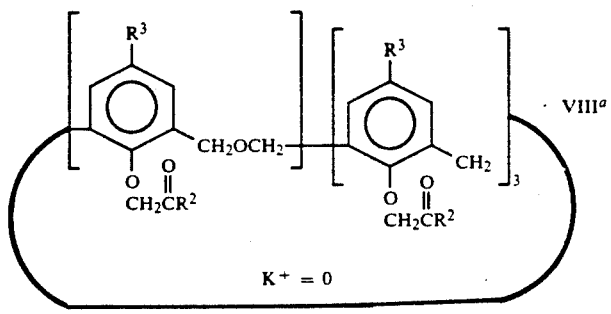

| Compound No. | R³ | R² | Slope | Na⁺ | Li⁺ | Cs⁺ | Rb⁺ | NH₄⁺ | H⁺ | Ca²⁺ | Mg²⁺ |
|---|---|---|---|---|---|---|---|---|---|---|---|
| 60 | t-Bu | OCH₂CH₃ | 56.5 | −1.5 | −2.9 | −0.9 | −0.5 | −1.6 | −3.3 | −3.1 | −2.6 |
| 60* | t-Bu | OCH₂CH₃ | 52.75 | −1.4 | −2.5 | −1.2 | −1.9 | −1.8 | −2.9 | −2.5 | −2.3 |
| XXI | t-Bu | SCH₂CH₃ | 55.65 | −1.4 | −2.2 | +0.7 | +0.3 | −0.6 | −1.6 | −2.3 | −1.9 |
| XXVII | t-Bu | Ot-Bu | 53.00 | −1.9 | −3.2 | −0.7 | −0.3 | −1.4 | −1.6 | −2.9 | −2.1 |
| XXVI | t-Bu | OCH₂CH₂OCH₃ | 55.20 | −1.2 | −1.9 | +0.1 | −0.2 | −1.0 | −1.6 | −1.6 | −1.8 |

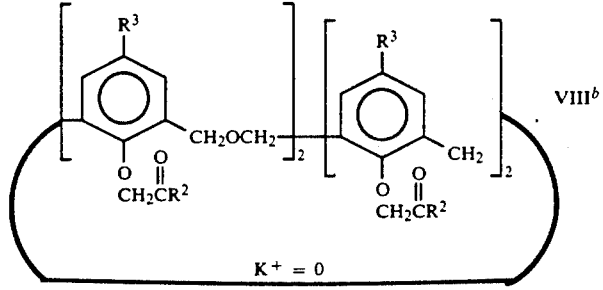

| Compound No. | R³ | R² | Slope | Na⁺ | Li⁺ | Cs⁺ | Rb⁺ | NH₄⁺ | H⁺ | Ca²⁺ | Mg²⁺ |
|---|---|---|---|---|---|---|---|---|---|---|---|
| XVIII | t-Bu | Ot-Bu | 55.30 | −1.5 | −2.4 | −0.1 | −0.4 | −0.6 | −0.5 | −1.3 | −1.2 |
| 61 | t-Bu | OCH₂CH₃ | 54.60 | −1.5 | −1.9 | −0.1 | 0 | 0.4 | — | −1.2 | −0.8 |
| XX | t-Bu | OCH₂CH₂OCH₃ | 54.80 | −1.8 | −3.3 | −1.0 | −1.1 | −1.2 | −2.8 | — | — |
| XIX | t-Bu | CH₃ | 55.72 | −1.5 | −2.6 | −0.1 | −0.1 | −0.9 | −1.8 | −2.9 | −2.9 |
| XXII | t-Bu | SCH₂CH₃ | 55.43 | −1.6 | −2.2 | +0.6 | +0.3 | −0.8 | −2.2 | −2.3 | −2.0 |

Selectivity for caesium-selective Electrodes

| Compound No. | R³ | R² | Slope | Li⁺ | Na⁺ | K⁺ | Rb⁺ | Mg²⁺ | Ca²⁺ | H⁺ | NH₄⁺ |
|---|---|---|---|---|---|---|---|---|---|---|---|

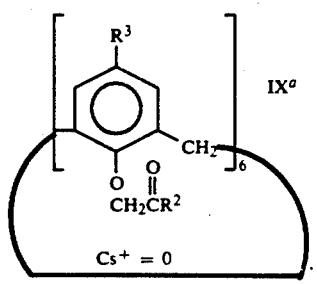

| Compound No. | R³ | R² | Slope | Li⁺ | Na⁺ | K⁺ | Rb⁺ | Mg²⁺ | Ca²⁺ | H⁺ | NH₄⁺ |
|---|---|---|---|---|---|---|---|---|---|---|---|
| 62 | allyl | OCH₂CH₃ | | −3.4 | −2.1 | −0.9 | −0.6 | −3.6 | −3.6 | −2.4 | −1.7 |
| 42* | t-Bu | OCH₂CH₃ | 54.0 | −3.3 | −2.1 | −0.7 | −1.2 | −2.8 | −3.6 | −2.0 | −1.9 |
| 41* | H | OCH₂CH₃ | 51.3 | −4.2 | −3.9 | −2.7 | −1.9 | −4.0 | −3.4 | −3.7 | −2.8 |

-continued

| | | | | | | | | | | |
|---|---|---|---|---|---|---|---|---|---|---|
| 40 | H | OCH$_3$ | 57.0 | −3.1 | −3.0 | −2.5 | −1.4 | — | — | −2.2 | −2.6 |
| XXX | t-Bu | OCH$_2$CH$_2$OCH$_3$ | 51.15 | −3.1 | −2.6 | −1.4 | −1.4 | −3.3 | −2.9 | −3.5 | −2.6 |
| XXIX | t-Bu | SCH$_2$CH$_3$ | 58.32 | −3.3 | −1.8 | −1.0 | −0.7 | −2.8 | −2.8 | — | −2.0 |
| XXXI | t-Bu | t-Bu | 57.15 | −1.8 | −0.6 | 0 | −0.2 | −1.6 | −2.6 | −2.3 | −1.0 |

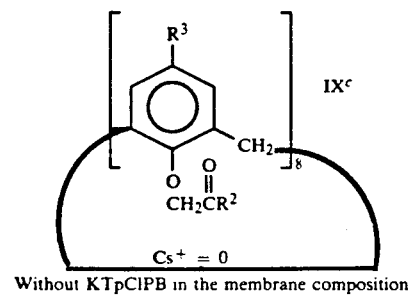

Without KTpClPB in the membrane composition

| | | | | | | | | | | |
|---|---|---|---|---|---|---|---|---|---|---|
| XXV | t-Bu | OCH$_2$CH$_2$OCH$_3$ | 47.88 | −2.4 | −0.9 | −0.4 | +0.2 | −1.4 | −1.0 | −0.8 | −0.6 |
| XXXII | t-Bu | t-Bu | 52.55 | −1.7 | −0.9 | +0.3 | +0.2 | −1.6 | −2.1 | −0.4 | −0.8 |

*No KTpClPB in the membrane composition

Selectivity Compound XV$^a$ K$^+$ = 0
Partial cone

| Slope | Na$^+$ | Li$^+$ | Cs$^-$ | Rb$^+$ | NH$_4^+$ | H$^+$ | Ca$^{2+}$ | Mg$^{2+}$ |
|---|---|---|---|---|---|---|---|---|
| 58.64 | −0.2 | −1.9 | −1.3 | −0.8 | −1.7 | −2.7 | −2.6 | −1.8 |

Selectivity Compound XXIV Cs$^+$ = 0
(heptamer)

| Slope | Li$^+$ | Na$^-$ | K$^+$ | Rb$^-$ | Mg$^{2+}$ | Ca$^{2-}$ | H$^+$ | NH$_4^+$ |
|---|---|---|---|---|---|---|---|---|
| 56.00 | −2.4 | −1.4 | −0.5 | −0.2 | −2.3 | −2.7 | −2.0 | −1.5 |

Selectivity Compound XXXIV K$^+$ = 0
Partial cone

| Slope | Na$^+$ | Li$^+$ | Cs$^+$ | Rb$^+$ | NH$_4^-$ | H$^-$ | Ca$^{2+}$ | Mg$^{2+}$ |
|---|---|---|---|---|---|---|---|---|
| 58.0 | −0.7 | −2.0 | −0.6 | −0.6 | −1.5 | −2.6 | −2.6 | — |

Triethylacetate of 7,15,23,-Tri-tert.-butyl-2,3,10,11,18,19-hexahomo-3,11,19-trioxacalix(3)arene, prepared as in U.S. Pat. No. 4,855,461 Harris et. al., mp 151°-3° C.

Selectivity K$^+$ = 0

| Slope | Na$^+$ | Li$^+$ | Cs$^+$ | Rb$^+$ | NH$_4^+$ | H$^+$ | Ca$^{2+}$ | Mg$^{2+}$ |
|---|---|---|---|---|---|---|---|---|
| 60.14 | −1.7 | −2.1 | 0 | +0.3 | −0.8 | −2.6 | −2.8 | −1.8 |

Compound 50 (oxime)
Selectivity
Na$^+$ = 0

| K$^+$ | Li$^+$ | Cs$^+$ | Rb$^+$ | H$^+$ | Ca$^{2+}$ | Mg$^{2+}$ |
|---|---|---|---|---|---|---|
| −0.8 | −0.8 | −1.3 | −1.2 | — | −1.1 | −1.1 |

This oxime is suitable for a non-specific ion-selective electrode.

We claim:

1. An ion-selective polymeric membrane for an electrochemical sensor comprising
   a) a supporting matrix, and
   b) an ionophore selected from calixarene or oxacalixarene derivatives of the formula IV

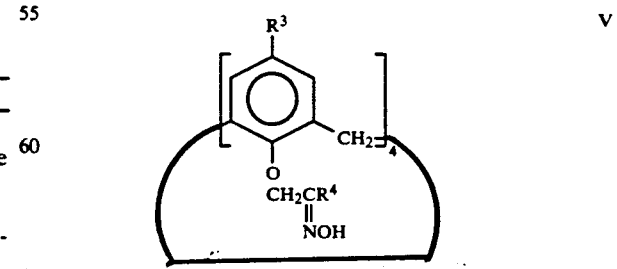

wherein
n+m=3-8;
m=0-8;
n=0-8;
a, which may be the same or different on each aryl group, is 0 or 1;
R$^2$ is alkyl, aryl, alkaryl, alkoxy, alkoxyalkoxy, aryloxy, alkaryloxy, alicyclic, alkylthio, arylthio, alkarylthio, or a substituted derivative thereof;
R$^3$ is —H, alkyl or alkenyl;
X is —OH or a group containing an acrylate or methacrylate functional group;
provided that when X is —OH, n is at least ½(n+m);
and provided that when m=0, n=4, a=0 and R$^3$ is alkyl or allyl, R$^2$ is not alkoxy having 4 or more carbon atoms in the alkyl group;
and provided that when m=0, n=4, a=0 and R$^3$ is t-butyl, R$^2$ is not alkoxy having 1 to 3 carbon atoms in the alkyl group;
or of the formula V

V wherein R$^4$ is alkyl; or polymers of those compounds of the formula IV in which X is a group containing an acrylate or methacrylate group.

2. A membrane according to claim 1 wherein the ionophore is a compound of formula IV in which
R$^2$ is —[O(CH$_2$)$_{n'}$]$_{n''}$O C$_{m'}$ H$_{2m'+1}$ wherein
n'=1-5,
m'=1-5,
n''=0 or 1.

3. A membrane according to claim 1 wherein the ionophore is a compound of formula IV in which
R$^2$ is —[OCH$_2$C(O)]$_{n''}$—C$_6$H$_5$ wherein n'' is as defined in claim 2.

4. A membrane according to claim 1 wherein the ionophore is a compound of formula IV in which
R$^2$ is —SC$_{m'}$ H$_{2m'+1}$ wherein m' is as defined in claim 2.

5. A membrane according to claim 2 wherein the ionophore is a compound of formula IV in which
R$^3$ is H, and
R$^2$ is —OC$_{m'}$ H$_{2m'+1}$
wherein m' is as defined in claim 2.

6. A membrane according to claim 1 wherein the ionophore is a compound of formula IV in which X is of the formula

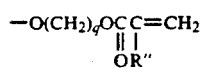

wherein
q=an integer 2-10 and
R'' is H or CH$_3$.

7. A sodium-selective membrane according to claim 1 wherein the ionophore is a calixarene derivative of the formula VI$^a$

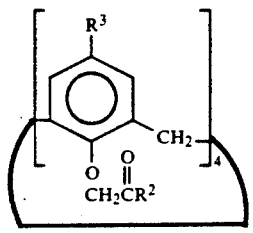

in cone conformation,
wherein R$^2$ and R$^3$ are as defined in claim 1, or of the formula VII

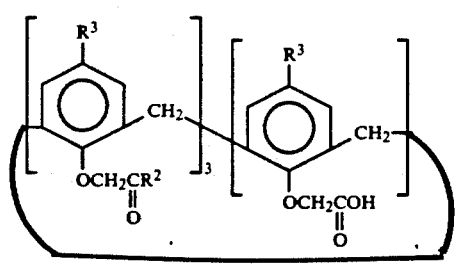

wherein R$^2$ and R$^3$ are as defined in claim 1.

8. A potassium-selective membrane according to claim 1 wherein the ionophore is a calixarene derivative of the formula VI$^b$

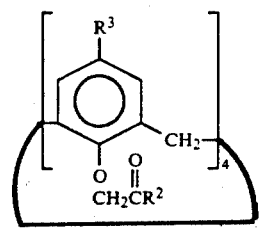

in partial cone conformation, wherein R$^2$ and R$^3$ are as defined in claim 1 or an oxacalixarene derivatives of the formula VIII$^a$

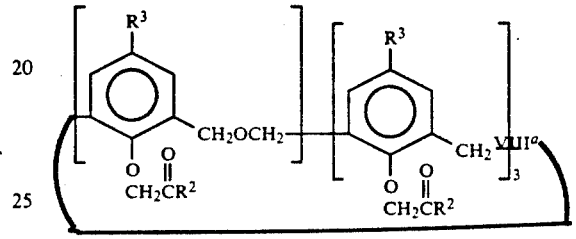

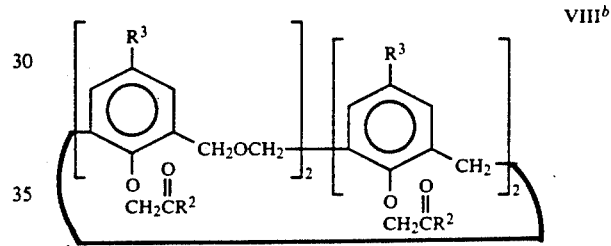

or

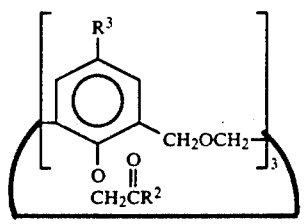

wherein R$^2$ and R$^3$ are as defined in claim 1.

9. A caesium-selective membrane according to claim 1 wherein the ionophore is a calixarene derivative of the formula IX$^a$

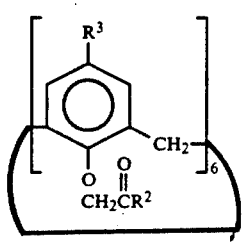

or of the formula IX$^b$

-continued

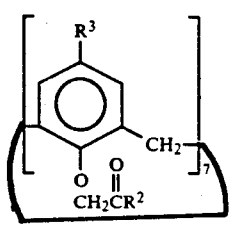

or of the formula IX$^c$

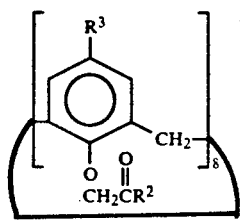

wherein R$^2$ and R$^3$ are as defined in claim 1.

10. A membrane according to claim 1 wherein the membrane composition further comprises potassium tetra-parachlorophenyl borate (KTpClPB) as an ion-exchanger.

11. A member according to claim 1 wherein the membrane composition contains a plasticiser selected from 2-nitrophenyl octyl ether, dioctylphthalate, dibutyl-sebacate or dioctylphenylphosphonate.

12. Calixarene or oxacalixarene derivatives of the formula IV$^a$

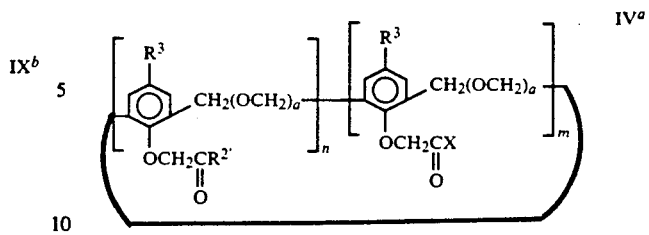

wherein
n+m=3-8;
m=0-8;
n=0-8;
a, which may be the same or different on each aryl group, is 0 or 1;
R$^{2'}$ is alkylthio, arylthio, alkarylthio, or a substituted derivative thereof;
R$^3$ is —H, alkyl or alkenyl;
X is OH or a group containing an acrylate or methacrylate functional group;
provided that when X is —OH, n is at least ½ (n+m);

13. Compounds according to claim 12 wherein R$^{2'}$ is —SC$_{m'}$H$_{2m'+1}$ wherein m' is 1-5.

14. An ion selective electrochemical sensor having a membrane according to claim 1.

15. A membrane according to claim 1 wherein the ionophore is a compound of formula IV in which when m=0, n=6 and a=0, R$^2$ is not ethoxy.

16. A membrane according to claim 7 wherein the ionophore is a compound of the formula VI$^a$ wherein R$^3$ is H.

17. A membrane according to claim 7 wherein the ionophore is a compound of the formula VI$^a$ wherein R$^3$ is t-butyl and R$^2$ is selected from C$_1$-C$_5$ alkyl, aryl, alkaryl, phenoxy or benzyloxy or a phenyl ring-substituted derivative thereof.
—OCH$_2$CH$_2$OCH$_3$,

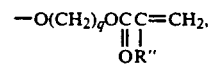

wherein q=an integer 2-10 and R" is H or CH$_3$, —O CH$_2$ C (O) C$_6$H$_5$ or phenyl ring-substituted derivative thereof, or —O CH$_2$ CH$_2$ Y
wherein Y is a nitrogen-containing heterocyclic radical.

* * * * *